(12) United States Patent
Akizumi et al.

(10) Patent No.: US 8,394,869 B2
(45) Date of Patent: Mar. 12, 2013

(54) PHOTOPOLYMERIZABLE COMPOSITIONS USEFUL AS A DENTAL RESTORATIVE MATERIAL

(75) Inventors: Hironobu Akizumi, Tokyo (JP); Junichiro Yamagawa, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 143 days.

(21) Appl. No.: 12/991,251

(22) PCT Filed: May 20, 2009

(86) PCT No.: PCT/JP2009/059250
§ 371 (c)(1),
(2), (4) Date: Dec. 14, 2010

(87) PCT Pub. No.: WO2009/142229
PCT Pub. Date: Nov. 26, 2009

(65) Prior Publication Data
US 2011/0172323 A1   Jul. 14, 2011

(30) Foreign Application Priority Data
May 21, 2008 (JP) ................................. 2008-132956

(51) Int. Cl.
*C08G 59/68* (2006.01)
*A61L 27/34* (2006.01)
*C08F 2/50* (2006.01)

(52) U.S. Cl. ................ 522/31; 522/48; 522/59; 522/63; 522/77; 522/83; 523/115; 523/116; 523/117; 523/118; 433/228.1

(58) Field of Classification Search .................... 522/31, 522/48,59, 63, 77, 83; 523/115–118; 433/228.1
See application file for complete search history.

(56) References Cited

U.S. PATENT DOCUMENTS

| 3,819,568 | A * | 6/1974 | Taylor et al. ................... 523/116 |
| 6,262,142 | B1 * | 7/2001 | Wang et al. .................... 523/116 |
| 6,353,040 | B1 * | 3/2002 | Subelka et al. ................ 523/116 |
| 2006/0148813 | A1 * | 7/2006 | Tully et al. ................ 514/252.16 |
| 2009/0005469 | A1 * | 1/2009 | Craig et al. ...................... 522/78 |
| 2010/0297588 | A1 * | 11/2010 | Kalgutkar et al. .......... 433/228.1 |
| 2011/0200971 | A1 * | 8/2011 | Kalgutkar et al. .......... 433/201.1 |

FOREIGN PATENT DOCUMENTS

| JP | 2001-524113 A | 11/2001 |
| JP | 2002-520347 A | 7/2002 |
| JP | 2002-370916 A | 12/2002 |
| JP | 2004-231913 A | 8/2004 |
| JP | 2005-89729 A | 4/2005 |
| JP | 2005-213231 A | 8/2005 |
| JP | 2006-117543 A | 5/2006 |
| JP | 2006-241114 A | 6/2006 |
| JP | 2007-231210 A | 9/2007 |

OTHER PUBLICATIONS

International Search Report, dated Jul. 23, 2009.

* cited by examiner

*Primary Examiner* — Nathan M Nutter
(74) *Attorney, Agent, or Firm* — Norris McLaughlin & Marcus PA

(57) ABSTRACT

Disclosed are photopolymerizable compositions suitable for uses such as dental composite resins, and that comprise (A) a radical-polymerizable monomer, (B) a photopolymerization initiator that comprises (B1) an α-diketone compound, (B2) a photoacid generating agent, (B3) an aromatic amine compound, and (C) an organic filler containing a phthalate ester fluorescent agent.

7 Claims, No Drawings

PHOTOPOLYMERIZABLE COMPOSITIONS USEFUL AS A DENTAL RESTORATIVE MATERIAL

This application is a 371 application of PCT/JP2009/059250 filed May 20, 2009, which claims foreign priority benefit under 35 U.S.C. §119 of Japanese application 2008-132956 filed May 21, 2008.

TECHNICAL FIELD

The present invention relates to a photopolymerizable composition, particularly to a photopolymerizable composition useful as a dental restorative material.

BACKGROUND ART

In dental treatment, various tooth restorative materials are being used. For example, in restoring the tooth damaged by decay, breakage or the like, pasty restorative composite materials for filling, generally called composite resin are in wide use. This composite resin ordinarily comprises a polymerizable monomer, a filler, a photopolymerization initiator, etc. and is photo-curable. With this composite resin, the restorative operation of tooth is simple and the tooth after restoration is beautiful.

The pasty composite resin comprising a photopolymerization initiator is required to hardly cure in an environmental light until it is used. Further, the pasty composite resin, when used, is required to be cured rapidly by strong light application using a light applicator or the like. However, any of conventional composite resins has had no sufficiently good balance between the stability to environmental light and the high reactivity to applied light. That is, there has been developed yet no pasty composite resin which causes no cure by a weak light such as environmental light and is cured rapidly by a strong light of light applicator or the like.

In order to solve the above problem, the present inventors made studies on novel photopolymerization initiators. As the result of the studies, the present inventors found a photopolymerization initiator comprising an α-diketone compound, a photoacid generating agent and an amine compound and proposed it (Patent Documents 1 and 2). Incidentally, as the amine compound, there is preferably used an aromatic amine from the standpoints of the high polymerization activity, etc.

The photopolymerization initiator developed by the present inventors is not activated when irradiated with a weak light (e.g. an environmental light) (below 1 mW/cm$^2$ at 360 to 500 nm), whereby a pasty composite resin comprising this photopolymerization initiator is protected from polymerization. Meanwhile, when irradiated with a strong light by a light applicator such as halogen lamp, xenon lamp or the like, the pasty composite resin completes polymerization in a very short time. The composite resin containing the photopolymerization initiator is cured rapidly when irradiated with a strong light, and the cured material obtained has good properties. Therefore, the photopolymerization initiator enables production of a dental composite resin having good properties.

In restoration of tooth by using a conventional dental composite resin, it is generally possible to conduct a restoration in which the restored site harmonizes with neighboring teeth in such an extent that the site is difficult to distinguish and the restored site is beautiful. However, the restored site looks blackish in an environment where an ultraviolet light or a visible light of short wavelength is applied, and the person having a restored tooth is forced to have a mental burden.

In order to alleviate this drawback, it was proposed to compound a fluorescent agent in a dental composite resin. As the fluorescent agent compounded, a phthalate ester fluorescent agent is easy to procure, emits a fluorescence similar to natural teeth, and gives an excellent beauty. Therefore, this fluorescent agent is being used advantageously (see, for example, Patent Document 3).
Patent Document 1: JP2005-89729A
Patent Document 2: JP2005-213231A
Patent Document 3: National Publication of International Patent Application-2002-520347

DISCLOSURE OF THE INVENTION

Technical Problem

The study by the present inventors found that, when a dental composite resin was produced by compounding the above-mentioned photopolymerization initiator (comprising an α-diketone compound, a photoacid generating agent and an aromatic amine compound) and a phthalate ester fluorescent agent, the polymerization activity of the photopolymerization initiator compounded in the dental composite resin decreased strikingly during the storage of the dental composite resin. The further study by the present inventors found that the decrease in the polymerization activity might cause a problem in the actual use of the dental composite resin.

Specifically explaining, when the dental composite resin is stored at about 30° C., the polymerization activity thereof decreases strikingly. In the delivery of dental materials to a dental clinic or the like, they are carried by a private car or the like, in many cases. In the summer, it is not rare that the temperature inside the car exceeds 50° C. In such a situation, the polymerization activity of the photopolymerization initiator decreases greatly for the above-mentioned reason. Consequently, the dental composite resin tends to lose its commercial value.

The present inventors thought that the decrease in the polymerization activity of the dental composite resin is caused by the reaction of the phthalate ester fluorescent agent compounded in the dental composite resin, with the photoacid generating agent also compounded in the dental composite resin and by the resultant loss of the photoacid generating ability.

The task of the present invention is to provide a photopolymerizable composition, for example, a dental composite resin comprising, in combination, the above-mentioned photopolymerization initiator (comprising an α-diketone compound, a photoacid generating agent and an aromatic amine compound) and a phthalate ester fluorescent agent, wherein the photopolymerization activity of the photopolymerization initiator is kept satisfactorily and the fluorescence of the phthalate ester fluorescent agent is expressed satisfactorily.

Technical Solution

The present inventors made a study in order to achieve the above task. As a result, it was found that the above task could be achieved by compounding a phthalate ester fluorescent agent in a photopolymerizable composition in a state that the phthalate ester fluorescent agent was contained in an organic filler. The finding has led to the completion of the present invention.

The present invention is a photopolymerizable composition comprising
(A) a radical-polymerizable monomer,
(B) a photopolymerization initiator comprising (B1) an α-diketone compound,
(B2) a photoacid generating agent, and
(B3) an aromatic amine compound, and
(C) an organic filler containing a phthalate ester fluorescent agent.

Effect of the Invention

The photopolymerizable composition of the present invention is highly stable to a weak light (below 1 mW/cm$^2$) such as environmental light or the like. Meanwhile, it completes polymerization in a very short time when irradiated with a strong light (at least 100 mW/cm$^2$) of a light applicator such as halogen lamp, xenon lamp or the like. The photopolymerizable composition of the present invention has fluorescence and the excellent polymerization activity thereof hardly decreases even when the composition is stored over a long period, particularly for a long period at a high temperature. Therefore, the photopolymerizable composition of the present invention is very useful as a photopolymerizable composition used in a dental restorative material such as dental composite resin, hard resin or the like.

BEST MODE FOR CARRYING OUT THE INVENTION

Description is made below on each component of the photopolymerizable composition of the present invention.
[(A) Radical-Polymerizable Monomer]

As the radical-polymerizable monomer, known such monomers can be used with no particular restriction. As examples of the monomer generally used preferably, there can be mentioned the monomers represented by the following (I) to (III).
(I) Bi-Functional Polymerizable Monomers
(i) Aromatic Compound Monomers Exemplary monomers include 2,2-bis(methacryloyloxyphenyl)propane, 2,2-bis[4-(3-methacryloyloxy)-2-hydroxypropoxyphenyl]propane (hereinafter abbreviated as bis-GMA), 2,2-bi(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4- methacryloyloxytetraethoxyphenyl)propane, 2,2-bis(4- methacyryloyloxypentaethoxyphenyl)propane, 2,2-bis(4-methacrylolyloxy dipropoxyphenyl)propane, 2(4-methacryloyloxy diethoxyphenyl)-2-(4- methacryloyloxytriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, and 2,2-bis(4-methacryloyloxyisopropoxyphenyl)propane; and acrylates corresponding to these methacrylates.

Exemplary monomers further include diadducts obtained by the addition reaction between —OH group-containing vinyl monomer and aromatic group-containing diisocyanate compound.

As the —OH group-containing vinyl monomer, there are preferred methacrylates such as 2-hydroxyethyl methacrylate, 2-hydroxypropyl methacrylate, 3-chloro-2-hydroxypropyl methacrylate and the like; and acrylates corresponding to these methacrylates.

As the aromatic group-containing diisocyanate compound, there are preferred diisocyanato methylbenzene, 4,4'-diphenylmethane diisocyanate, etc.

(ii) Aliphatic Compound Monomers

Exemplary monomers include ethylene glycol dimethacrylate, diethylene glycol dimethacrylate, triethylene glycol dimethacrylate (hereinafter abbreviated as 3G), tetraethylene glycol dimethacrylate, neopentyl glycol dimethacrylate, 1,3-butanediol dimethacrylate, 1,4-butanediol dimethacrylate, and 1,6-hexanediol dimethacrylate; and acrylates corresponding to these methacrylates.

Exemplary monomers further include diadducts which are addition products between —OH group-containing vinyl monomer and diisocyanate compound.

As the —OH group-containing vinyl monomer, there are preferred methacrylates such as 2-hydroxyethyl methacrylate, 2-hydroxypropyl methacrylate, 3-chloro-2-hydroxypropyl methacrylate and the like; and acrylates corresponding to these methacrylates.

As the diisocyanate compound, there are preferred hexamethylene diisocyanate, trimethylhexamethylene diisocyanate, diisocyanato methylcyclohexane, isophorone diisocyanate, methylenebis(4-cyclohexyl isocyanate), etc.

Exemplary monomers further include 1,2-bis(3-methacryloyloxy-2-hydroxypropoxy)ethyl, etc.
(II) Tri-Functional Polymerizable Monomers Exemplary monomers include methacrylates such as trimethylolpropane trimethacrylate, trimethylolethane trimethacrylate, pentaerythritol trimethacrylate, trimethylolmethane trimethacrylate and the like; and acrylates corresponding to these methacrylates.
(III) Tetra-Functional Polymerizable Monomers Exemplary monomers include pentaerythritol tetramethacrylate and pentaerythritol tetraacrylate.

Exemplary monomers further include diadducts which are addition products between diisocyanate compound (such as diisocyanato methylbenzene, diisocyanato methylcyclohexane, isophorone diisocyanate, hexamethylene diisocyanate, trimethylhexamethylene diisocyanate, methylenebis(4-cyclohexyl isocyanate), 4,4-diphenylmethane diisocyanate or tolylene-2,4-diisocyanate) and glycidol dimethacrylate.

Incidentally, the above-mentioned poly-functional (meth)acrylate polymerizable monomers may be used in combination of different kinds, as necessary.

Further, there may be used, as necessary, monofunctional (meth)acrylate monomers such as methacrylate (such as methyl methacrylate, ethyl methacrylate, isopropyl methacrylate, hydroxyethyl methacrylate, tetrahydrofurfuryl methacrylate or glycidyl methacrylate) and acrylate corresponding to such a methacrylate.

Furthermore, there may be used appropriately polymerizable monomers other than the above-mentioned (meth)acrylate monomers.

Incidentally, in the photopolymerizable composition of the present invention, the photopolymerization initiator (B) comprises, as described later, (B3) an aromatic amine compound as an essential component. The aromatic amine compound (B3) forms a salt upon reaction with an acid. In this case, the photopolymerization initiator (B) tends to lose the polymerization activity. Therefore, it is preferred that an acid group-containing polymerizable monomer is not used as the radical-polymerizable monomer (A) except when it is present inevitably as an impurity or the like, of the (meth)acrylate monomer or the like. As the acid group-containing polymerizable monomer, there can be mentioned, for example, (meth)acrylic acid, p-(meth)acryloyloxybenzoic acid, 10-methacryloyloxydecamethylenemalonic acid, and 2-hydroxyethyl hydrogenphenyl phosphate.

When the amount of the acid group-containing polymerizable monomer present is an ordinary impurity amount as mentioned above, the polymerization activity of the photopolymerization initiator can be kept by compounding the aromatic amine compound in a slight excess. In this case, the appropriate compounding amount of the aromatic amine compound is an amount including the amount of the aromatic amine compound neutralized by the acid of impurity amount present.

[(B) Photopolymerization Initiator]

[(B1) α-Diketone Compound]

The photopolymerizable composition of the present invention includes (B) a photopolymerization initiator. The first component of the photopolymerization initiator is (B1) an α-diketone compound. As the α-diketone compound (B1), known such a compound can be used with no particular restriction. As specific examples of the α-diketone compound, there can be mentioned camphorquinones (e.g. camphorquinone), diacetyl, acetyl benzoyl, 2,3-pentadione, 2,3-octadione, 9,10-phenanthrenequinone, and acenaphthenequinone.

The α-diketone compound used is appropriately selected depending upon the wavelength and intensity of the light used for polymerization, the time of light application, and the kind and amount of the other components used in combination. The α-diketone compound may be used in one kind or in admixture of two or more kinds. As the α-diketone compound, there are generally preferred camphorquinones and particularly preferred camphorquinone.

The use amount of the α-diketone compound differs depending upon the kinds of the other components used in combination and the radical-polymerizable monomer used, but ordinarily is preferably 0.01 to 10 parts by mass, more preferably 0.03 to 5 parts by mass relative to 100 parts by mass of the radical-polymerizable monomer (A). Generally, as the use amount of the α-diketone compound is larger, the photopolymerizable composition is cured in a shorter time when irradiated with a light. Meanwhile, as the use amount of the α-diketone compound is smaller, the photopolymerizable composition is higher in stability to environmental light.

[(B2) Photoacid Generating Agent]

The second component of the photopolymerization initiator used in the photopolymerizable composition of the present invention is (B2) a photoacid generating agent.

The photoacid generating agent (B2) is a compound which can directly generate a Brønsted acid or a Lewis acid when irradiated with a light such as ultraviolet light or the like. As the photoacid generating agent (B2), a known compound can be used with no particular restriction.

As specific examples of the photoacid generating agents, there can be mentioned a diaryl iodonium salt compound, a sulfonium salt compound, a sulfonic acid ester compound, and a halomethyl group-substituted s-triazine compound.

As the halomethyl group-substituted s-triazine compound, there is preferred a trihalomethyl group-substituted s-triazine compound, because a higher polymerization activity is obtained. In the present invention, the most preferred photoacid generating agent is at least one kind selected from a trihalomethyl group-substituted s-triazine compound and a diaryl iodonium salt compound because very high polymerization activity can be obtained.

Representative trihalomethyl group-substituted s-triazine compounds are s-triazine compounds having at least one trihalomethyl group such as trichloromethyl group, tribromomethyl group or the like. As these compounds, known compounds can be used with no restriction. A particularly preferred trihalomethyl group-substituted s-triazine compound is represented by the following general formula (1).

[Formula 1]

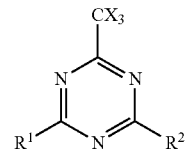

(In the formula, $R^1$ and $R^2$ are an alkyl group, an aryl group, an alkenyl group or an alkoxy group; and X is a halogen atom.)

In the above general formula (1), the halogen atom represented by X is preferably a chlorine, bromine or iodine atom. In these halogen atoms containing group, a trichloromethyl group-containing s-triazine compound is preferred.

$R^1$ and $R^2$ are an alkyl group, an aryl group, an alkenyl group or an alkoxy group and may be unsubstituted. $R^1$ and $R^2$ may be substituted with, for example, halogen or the group mentioned above as $R^1$ and $R^2$ but different from $R^1$ or $R^2$ itself.

As the alkyl group, there can be mentioned, for example, unsubstituted alkyl groups of 1 to 10 carbon atoms, such as methyl group, ethyl group, n-propyl group, isopropyl group, n-butyl group, n-hexyl group, n-octyl group and the like; and halogen-substituted alkyl groups of 1 to 10 carbon atoms, such as trichloromethyl group, tribromomethyl group, α,αβ-trichloroethyl group and the like.

As the aryl group, there can be mentioned, for example, aryl groups of 6 to 14 carbon atoms, such as phenyl group, p-alkoxyphenyl group (e.g. p-methoxyphenyl group), p-alkylthiophenyl group (e.g. p-methylthiophenyl group), p-halophenyl group (e.g. p-chlorophenyl group), 4-biphenylyl group, naphthyl group, 4-alkoxy-1-naphthyl group (e.g. 4-methoxy-1-naphthyl group) and the like.

As the alkenyl group, there can be mentioned alkenyl groups of 2 to 14 carbon atoms, such as vinyl group, allyl group, isopropenyl group, butenyl group, 2-phenylethenyl group and the like.

As the alkoxy group, there can be mentioned alkoxy groups of 1 to 10 carbon atoms, such as methoxy group, ethoxy group, butoxy group, hexoxy group, octoxy group and the like.

As specific examples of the trihalomethyl group-substituted triazine compound, there can be mentioned 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, and 2-(4-bihenylyl)-4,6-bis(trichloromethyl)-s-triazine.

The triazine compound may be used in one kind or in admixture of two or more kinds.

As the diaryl iodonium salt compound (hereinafter, this may be referred to simply as "iodonium salt compound") which is a photoacid generating agent preferably used in the present invention, a known compound can be used with no restriction.

As a representative diaryl iodonium salt compound, there can be mentioned a compound represented by the following general formula (2)

[formula 2]

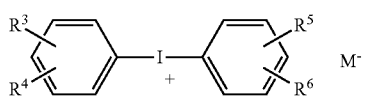

(2)

(in the above formula, $R^3$, $R^4$, $R^5$ and $R^6$ are each independently a hydrogen atom, a halogen atom, a nitro group, an alkyl group, an aryl group, an alkenyl group, an alkoxy group, an aryloxy group or a nitro group; and $M^-$ is a mono-valent anion).

When $R^3$, $R^4$, $R^5$ and $R^6$ are each a halogen atom, the halogen atom includes fluorine, chlorine, bromine and iodine.

When $R^3$, $R^4$, $R^5$ and $R^6$ are each an alkyl group, the alkyl group is preferably an alkyl group of 1 to 10 carbon atoms, such as methyl group, ethyl group, propyl group, isopropyl group, butyl group, sec-butyl group, pentyl group, isopentyl group, hexyl group, n-octyl group or the like.

When $R^3$, $R^4$, $R^5$ and $R^6$ are each an aryl group, the aryl group is preferably an aryl group of 6 to 14 carbon atoms, such as phenyl group, p-methylphenyl group, p-chlorophenyl group, naphthyl group or the like.

When $R^3$, $R^4$, $R^5$ and $R^6$ are each an alkenyl group, the alkenyl group is preferably an alkenyl group of 2 to 8 carbon atoms, such as vinyl group, allyl group, isopropenyl group, butenyl group or the like.

When $R^3$, $R^4$, $R^5$ and $R^6$ are each an alkoxy group, the alkoxy group is preferably an alkoxy group of 1 to 6 carbon atoms, such as methoxy group, ethoxy group, propoxy group, butoxy group or the like. As the aryloxy group, preferred are phenoxy, etc.

As to the mono-valent anion represented by $M^-$, there is no particular restriction. There can be specifically mentioned halogen anions such as chloride, bromide and the like; and ester anions such as p-toluenesulfonate, trifluoromethanesulfonate, tetrafluoroborate, tetrakispentafluorophenyl borate, tetrakispentafluorophenyl gallate, hexafluorophosphate, hexafluoroarsenate, hexafluoroantimonate and the like.

As specific examples of the diaryl iodonium salt represented by the above general formula (2), there can be mentioned diphenyl iodonium salts composed of a cation and an anion represented by the above $M^-$, such as diphenyl iodonium, bis(p-chlorophenyl)iodonium, ditolyl iodonium, bis(p-tert-butylphenyl) iodonium, p-isopropylphenyl-p-methylphenyl iodonium, bis(m-nitrophenyl) iodonium, p-tert-butylphenylphenyl iodonium, p-methoxyphenylphenyl iodonium, bis(p-methoxyphenyl) iodonium, p-octyloxyphenylphenyl iodonium and the like.

Of these diaryl iodonium salt compounds, preferred are, from the standpoint of the solubility in the radical-polymerizable monomer (A), p-toluenesulfonate, trifluoromethanesulfonate, tetrafluoroborate, tetrakispentafluorophenyl borate, tetrakispentafluorophenyl gallate, hexafluorophosphate, hexafluoroarsenate, and hexafluoroantimonate.

Particularly preferred are, from the standpoint of the storage stability, tetrakispentafluorophenyl borate, tetrakispentafluorophenyl gallate, and hexafluoroantimonate. These diaryl iodonium salt compounds may be used in one kind or in admixture of two or more kinds.

As the other photoacid generating agent preferably used in the photopolymerizable composition of the present invention, a sulfonium salt compound can be mentioned. As specific examples of the sulfonium salt compound, there can be mentioned chloride, bromide, p-toluenesulfonate, trifluoromethanesulfonate, tetrafluoroborate, tetrakispentafluorophenyl borate, tetrakispentafluorophenyl gallate, hexafluorophosphate, hexafluoroarsenate, hexafluoroantimonate salts of dimethylphenacylsulfonium, dimethylbenzylsulfonium, dimethyl-4-hydroxyphenylsulfonium, dimethyl-4-hydroxynaphthylsulfonium, dimethyl-4,7-dihydroxynaphthylsulfonium, dimethyl-4,8-dihydroxynaphthylsulfonium, triphenylsulfonium, p-tolyldiphenylsulfonium, p-tert-butylphenyldiphenylsulfonium, diphenyl-4-phenylthiophenylsulfonium, etc.

As still other photoacid generating agent, a sulfonic acid ester compound can be mentioned. As specific examples of the sulfonic acid ester compound, there can be mentioned benzoin tosylate, α-methylolbenzoin tosylate, o-nitrobenzyl p-toluenesulfonate, and p-nitrobenzyl-9,10-diethoxyanthracene-2-sulfonate.

These photoacid generating agents may be used in one kind or in combination of different kinds.

The use amount of the photoacid generating agent is generally 0.005 to 10 parts by mass, preferably 0.03 to 5 parts by mass relative to 100 parts by mass of the radical-polymerizable monomer (A).

[(B3) Aromatic Amine Compound]

The third component of the photopolymerization initiator compounded in the photopolymerizable composition of the present invention is (B3) an aromatic amine compound. In the aromatic amine compound, at least one of the organic groups bonding to the nitrogen atom is an aromatic group. As the aromatic amine compound, a known compound can be used with no particular restriction.

As the aromatic amine compound, there is preferred, in particular, an amine compound in which one aromatic group and two aliphatic groups are bonded to a tertiary nitrogen atom (hereinafter, the amine compound is referred also to as "tertiary aromatic amine compound"), because it gives a high polymerization activity, is low in odor due to the low volatility, and is easy to procure.

As a representative tertiary aromatic amine compound, a compound represented by the following general formula (3) can be mentioned.

[Formula 3]

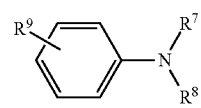

(3)

(In the formula, $R^7$ and $R^8$ are each independently an alkyl group; and $R^9$ is a hydrogen atom, an alkyl group, an aryl group, an alkenyl group, an alkoxy group or an alkyloxycarbonyl group.)

Each alkyl group represented by $R^7$ and $R^8$, or the alkyl group, aryl group, alkenyl group, alkoxy group or alkyloxycarbonyl group represented by $R^9$ may be unsubstituted. Or, $R^7$, $R^8$ and $R^9$ may be substituted with the substituent mentioned with respect to $R^1$ and $R^2$, or with hydroxyl group.

As the alkyl group, there can be mentioned unsubstituted alkyl groups such as methyl group, ethyl group, n-propyl group, isopropyl group, n-butyl group, n-hexyl group, n-octyl group and the like; halogen-substituted alkyl groups such as chloromethyl group, 2-chloroethyl group and the like; hydroxyl-substituted alkyl groups such as 2-hydroxyethyl group and the like; and so forth. The number of the carbon atoms of the alkyl group is preferably 1 to 10.

As the aryl group, there can be mentioned, for example, phenyl group, p-alkoxyphenyl (e.g. p-methoxyphenyl), p-alkylthiophenyl group (e.g. p-methylthiophenyl group), p-halophenyl group (e.g. p-chlorophenyl group), and 4-biphenylyl group. The number of the carbon atoms of the aryl group is preferably 6 to 12.

As the alkenyl group, there can be mentioned vinyl group, allyl group, 2-phenylethenyl group, etc. The number of the carbon atoms of the alkenyl group is preferably 2 to 12.

As the alkoxy group, there can be mentioned methoxy group, ethoxy group, butoxy group, hexoxy group, octoxy group, etc. The number of the carbon atoms of the alkoxy group is preferably 1 to 10.

As the alkyloxycarbonyl groups, there can be mentioned, for example, methoxycarbonyl group, ethoxycarbonyl group, butoxycarbonyl group, amyloxycarbonyl group, and isoamyloxycarbonyl group or the like. The number of the carbon atoms of the alkyloxy group portion of the alkyloxycarbonyl group is preferably 1 to 10.

Of the functional groups represented by $R^7$ and $R^8$, an alkyl group of 1 to 6 carbon atoms is more preferred, and an unsubstituted alkyl group of 1 to 3 carbon atoms is particularly preferred. As examples of such an alkyl group, there can be once more mentioned methyl group, ethyl group, n-propyl group, etc.

The position at which $R^9$ bonds to benzene ring, is preferably a para position relative to nitrogen atom. Further, $R^9$ is preferably an alkyloxycarbonyl group.

When an amine compound having an aromatic group to which an alkyloxycarbonyl group bonds, and (B4) a component described later are compounded in combination into a photopolymerization initiator, there can be obtained a photopolymerizable composition having high polymerization activity and excellent storage stability.

As the aromatic amine compound in which the above-mentioned alkyloxycarbonyl group ($R^9$) bonds at a para-position relative to the nitrogen atom, there can be mentioned, for example, methyl p-dimethylaminobenzoate, ethyl p-dimethylaminobenzoate, propyl p-dimethylaminobenzoate, amyl p-dimethylaminobenzoate, isoamyl p-dimethylaminobenzoate, ethyl p-diethylaminobenzoate, and propyl p-diethylaminobenzoate.

As other aromatic amine compound represented by the general formula (3), there can be mentioned N,N-dimethylaniline, N,N-dibenzylaniline, N,N-dimethyl-p-toluidine, N,N-diethyl-p-toluidine, N,N-di((β-hydroxyethyl)-p-toluidine, etc.

These aromatic amine compounds may be used in one kind or in admixture of two or more kinds.

In general, the use amount of the aromatic amine compound is preferably 0.01 to 5 parts by mass, more preferably 0.02 to 3 parts by mass relative to 100 parts by mass of the radical-polymerizable monomer (A).

[(B4) Tertiary Aliphatic Amine Compound]

The photopolymerization initiator compounded in the photopolymerizable composition of the present invention has, as mentioned above, a basic constitution comprising an α-diketone, a photoacid generating agent and an aromatic amine compound. The photopolymerization initiator compounded in the photopolymerizable composition of the present invention includes a photopolymerization initiator which further comprises, in addition to the above basic constitution, (B4) a tertiary aliphatic amine compound. By using the tertiary aliphatic amine compound (B4) in combination, higher polymerization activity can be obtained.

The tertiary aliphatic amine compound (B4) is a tertiary amine compound in which three saturated aliphatic groups bond to a nitrogen atom. Further, in the tertiary aliphatic amine compound (B4), hydrogen atoms of at least two saturated aliphatic groups are each substituted with an electron attractive group. By compounding the amine compound having saturated aliphatic groups to which electron attractive groups bond in the photopolymerization initiator (B), high polymerization activity and excellent storage stability can be obtained.

Each electron attractive group has an effect of attracting electron from the carbon atom of the saturated aliphatic group to which the electron attractive group bond. The electron attractive group may be any known electron attractive group. However, there are preferred, in view of the chemical stability, hydroxyl group, aryl group (e.g. phenyl group or naphthyl group), unsaturated aliphatic group (e.g. ethenyl group (vinyl group), 1-propenyl group or ethynyl group), fluorine atom, alkoxy group, carbonyl group, carbonyloxy group and cyano group. Of these, there are preferred aryl group, unsaturated aliphatic group and hydroxyl group because they are especially superior in compound stability, are easy to synthesize, and have high solubility in radical-polymerizable monomer. Hydroxyl group is preferred particularly.

As to each saturated aliphatic group having an electron attractive group, there is no particular restriction. It may be any saturated aliphatic group of straight chain type, branched chain type and cyclic type; however, a straight chain or branched chain saturated aliphatic group of 1 to 6 carbon atoms is preferred in view of the easiness of synthesis and procurement. As to the position and number of the electron attractive group, there is no particular restriction, either. However, as the electron attractive group bonds to a carbon atom closer to the nitrogen atom of amine, higher storage stability is obtained. Preferably, the electron attractive group bonds to a carbon atom bonding to the nitrogen atom (first position carbon atom of saturated aliphatic group) or bonds to a neighboring carbon atom (second position carbon atom of saturated aliphatic group).

As specific examples of the saturated aliphatic group to which an electron attractive group bonds, there can be mentioned a hydroxyl group-containing saturated aliphatic group (e.g. 2-hydroxyethyl group, 2-hydroxypropyl group, 2-hydroxybutyl group or 2,3-dihydroxypropyl group); a saturated aliphatic group to which an unsaturated aliphatic group (e.g. allyl group (ethenylmethyl group), 2-propinyl group (ethynylmethyl group) or 2-butenyl group) bonds; and a saturated aliphatic group to which an aryl group (e.g. benzyl group) bonds.

As to the saturated aliphatic group to which no electron attractive group bonds, there is no particular restriction. However, there is preferred a straight chain or branched chain alkyl group of 1 to 6 carbon atoms, such as methyl group, ethyl group, propyl group, butyl group or the like.

As examples of the tertiary aliphatic amine compounds having two saturated aliphatic groups to each of which an electron attractive group bonds, there can be mentioned N-dimethyldiethanolamine, N-ethyldiethanolamine, N-propyldiethanolamine, N-ethyldiallylamine and N-ethyldibenzylamine.

As examples of the tertiary aliphatic amine compound having three saturated aliphatic groups each substituted with an electron attractive group, there can be mentioned triethanolamine, tri(isopropanol)amine, tri(2-hydroxybutyl)amine, triallylamine and tribenzylamine.

These tertiary aliphatic amine compounds (B4) may be used in one kind or in admixture of two or more kinds.

Generally, the use amount of the tertiary aliphatic amine compound (B4) is preferably 0.005 to 5 parts by mass, more preferably 0.01 to 3 parts by mass relative to 100 parts by mass of the radical-polymerizable monomer (A).

The use amount of the aromatic amine compound (B3) and the tertiary aliphatic amine compound (B4) are, in the total thereof, preferably 0.015 to 10 parts by mass, more preferably 0.03 to 6 parts by mass relative to 100 parts by mass of the radical-polymerizable monomer. The mass ratio thereof is preferably (B3):(B4)=3:97 to 97:3, on mass basis.

The use amount of the photopolymerization initiator (the total amount of all components as the photopolymerization initiator) is preferably 0.03 to 20 parts by mass, more preferably 0.05 to 10 parts by mass, particularly preferably 0.1 to 3 parts by mass relative to 100 parts by mass of the radical-polymerizable monomer (A).

[(C) Organic Filler Containing Phthalate Ester Fluorescent Agent]

The biggest feature of the present invention lies in that the organic filler contains a phthalate ester fluorescent agent. By trapping a fluorescent agent in the organic filler, the degradation of a photoacid generating agent, which is caused by the reaction between the fluorescent agent and the photoacid generating agent, is suppressed. As a result, the polymerization activity of the photopolymerization initiator decreases hardly. That is, even when the photopolymerization initiator comprising an α-diketone compound, a photoacid generating agent and an aromatic amine compound is used together with the phthalate ester fluorescent agent, the degradation of the photoacid generating agent by the phthalate ester fluorescent agent occurs hardly. For this reason, the photopolymerization initiator used in the present invention can keep high polymerization activity.

The organic filler used in the photopolymerizable composition of the present invention may be produced by any method as long as it is obtained by compounding a phthalate ester fluorescent agent in an organic resin matrix. An organic filler produced by the following method is preferred because it is easy to produce. That is, first, a polymerizable monomer and a phthalate ester fluorescent agent are mixed at given proportions using a mixer or the like, to obtain a mixture thereof. Then, the mixture is subjected to heating, light irradiation or the like, for polymerization. Thereafter, the polymer is ground to a desired grain size to obtain an organic filler.

As the phthalate ester fluorescent agent compounded in the organic filler, a known phthalate ester fluorescent agent can be used with no restriction. A particularly preferred phthalate ester fluorescent agent is represented by the following general formula (4).

[Formula 4]

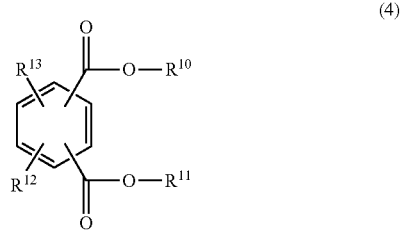

(4)

(In the formula, $R^{10}$ and $R^{11}$ are each independently an alkyl group; $R^{12}$ is a hydrogen atom, an amino group or a hydroxyl group; and $R^{13}$ is an amino group or a hydroxyl group.)

The alkyl group is preferably an alkyl group of 1 to 3 carbon atoms, such as methyl group, ethyl group, n-propyl group, isopropyl group or the like, more preferably an alkyl group of 1 to 2 carbon atoms.

As examples of the phthalate ester fluorescent agent, there can be mentioned dimethyl 2,5-dihydroxyterephthalate, diethyl 2,5-dihydroxyterephthalate, dimethyl aminoterephthalate, and diethyl aminoterephthalate. A hydroxyl group-containing phthalate ester fluorescent agent such as diethyl 2,5-dihydroxyterephthalate or the like is preferred. These phthalate ester fluorescent agents may be used singly or in admixture of two or more kinds.

The amount of the phthalate ester fluorescent agent used in the organic filler is not restricted particularly. The phthalate ester fluorescent agent is used in an amount of ordinarily 0.0001 to 5 parts by mass, preferably 0.001 to 0.5 mass part, more preferably 0.005 to 0.05 mass part relative to 100 parts by mass of the organic resin constituting the organic filler.

When an organic filler containing more than 5 parts by mass of the phthalate ester fluorescent agent is used in a dental restorative composite material such as photo-curable composite resin or the like, the cure material formed may be insufficient in properties such as strength, color and the like. Further, since the phthalate ester fluorescent agent is present in a high concentration on the surface of the organic filler, the fluorescent agent contacts with the polymerization initiator at a higher extent. Furthermore, the phthalate ester fluorescent agent dissolves into the photopolymerizable composition surrounding the organic filler, at a higher possibility. As a result, the storage stability of polymerization activity (which is the biggest feature of the present invention) may decrease.

When the use amount of the phthalate ester fluorescent agent is less than 0.0001 mass part, it is necessary to increase the use amount of the organic filler in order to obtain a sufficient fluorescence. In this case, paste properties (e.g. viscosity) are affected. Consequently, operability of restoration may decrease when there is used, in a dental restorative material or the like, a photopolymerizable composition using an organic filler containing a phthalate ester fluorescent agent in an amount of less than 0.0001 mass part.

The raw material monomer used in production of the organic filler may be any known polymerizable monomer. As the raw material monomer used preferably, a (meth)acryloyl group-containing monomer can be mentioned. As specific examples of such a polymerizable monomer, there can be mentioned those monomers mentioned as examples of the radical-polymerizable monomer (A). These radical-polymerizable monomers may be used singly or in admixture of different kinds.

In producing the organic filler, first, a polymerizable monomer, a phthalate ester fluorescent agent, etc. are mixed; then, the monomer is polymerized using a polymerization initiator, to obtain a cured material. Generally, as the polymerization initiator, an appropriate kind may be used depending upon the method used for polymerization of polymerizable monomer. The polymerization method includes a method using a light energy such as ultraviolet light, visible light or the like; a method using a chemical reaction between peroxide and accelerator; a method by heating; and so forth. The polymerization initiator is selected appropriately depending upon the polymerization method employed.

As the polymerization initiator used in curing of monomer in production of organic filler, a known polymerization initiator can be used with no particular restriction. A thermal polymerization initiator is preferably used because it can give an organic filler lower in yellow color.

As the polymerization initiator usable in the thermal polymerization, there can be mentioned, for example, peroxides such as benzoyl peroxide, p-chlorobenzoyl peroxide, tert-butyl peroxy-2-ethylhexanoate, tert-butyl peroxydicarbonate, diisopropyl peroxydicarbonate and the like; azo compounds such as azobisisobutyronitrile and the like; boron compounds such as tributylborane, partial oxidation product of tributylborane, sodium tetraphenylborate, sodium tetrakis (p-fluorophenyl)borate, triethanolamine salt of tetraphenylboric acid and the like; barbituric acids such as 5-butylbarbituric acid, 1-benzyl-5-phenylbarbituric acid and the like; and sulfinic acid salts such as sodium benzenesulfinate, sodium p-toluenesulfinate and the like.

As the polymerization initiator using light energy reaction (this reaction is hereinafter referred to as photopolymerization), there can be used, for example, benzoin alkyl ethers such as benzoin methyl ether, benzoin ethyl ether, benzoin isopropyl ether and the like; benzyl ketals such as benzyl dimethyl ketal, benzyl diethyl ketal and the like; benzophenones such as benzophenone, 4,4'-dimethylbenzophenone, 4-methacryloxybenzophenone and the like; α-diketones such as diacetyl, 2,3-pentadionebenzyl, camphorquinone, 9,10-phenanthraquinone, 9,10-anthraquinone and the like; thioxanthone compounds such as 2,4-diethoxythioxanthone, 2-chlorothioxanthone, methylthioxanthone and the like; and bisacylphosphine oxides such as bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis(2,4,6-trimethylbenzoyl)-phenylphosphine oxide and the like.

Incidentally, a reducing agent is often added to the photopolymerization initiator. As the reducing agent, there can be mentioned, for example, tertiary amines such as 2-(dimethylamino)ethyl methacrylate, ethyl 4-dimethylaminobenzoate, N-methyldiethanolamine and the like; aldehydes such as lauryl aldehyde, dimethylaminobenzaldehyde, terephthalaldehyde and the like; and sulfur-containing compounds such as 2-mercaptobenzoxazole, 1-decanethiol, thiosalicylic acid, thiobenzoic acid and the like.

These polymerization initiators may be used singly or in admixture of two or more kinds. The use amount of the polymerization initiator is determined depending upon the application purpose of the photopolymerizable composition; however, the amount is ordinarily 0.01 to 10 parts by mass, preferably 0.1 to 5 parts by mass relative to 100 parts by mass of the raw material monomer of the organic filler.

In producing the organic filler, a polymerizable monomer, a phthalate ester fluorescent agent, etc. are mixed; then, the monomer is polymerized using the above-mentioned polymerization initiator to obtain a cured material. The cured material is ground to obtain an organic filler.

In grinding the cured material, a vibration ball mill, a jet mill or the like can be used appropriately. By further conducting a classification step using a sieve, an air classifier, a water elutriator or the like, there can be obtained an organic filler having an intended grain size distribution. The organic filler used in the present invention has an average particle diameter of preferably 2 to 100 μm, more preferably 5 to 40 μm, from the standpoints of the mechanical strength of the organic filler and the operability when used as a curable paste In the organic filler, a known additive may be used besides the phthalate ester fluorescent agent, the raw material monomer of organic filler and the polymerization initiator, as long as the effect of the organic filler is not impaired. As such an additive, a pigment, a polymerization inhibitor, etc. can be mentioned.

When the organic filler is used in a dental restorative material (e.g. photo-curable composite resin), it is possible to add inorganic particles to the organic filler (the resulting filler may be hereinafter referred also to as inorganic-containing organic filler), for the higher mechanical strength of organic filler.

As the inorganic particles used as a raw material of the inorganic-containing organic filler, known inorganic particles can be used with no restriction. The material thereof is not restricted particularly; and there can be mentioned, for example, inorganic oxides such as amorphous silica, silica zirconia, silica titania, silica titania barium oxide, quartz, alumina and the like. These inorganic oxides may be composite oxides obtained by compounding a small amount of an oxide of a metal of group I of periodic table in the above-mentioned inorganic oxide, in order to easily obtain a dense inorganic oxide by high-temperature firing. The material of inorganic particles is preferred to be, in particular, a composite oxide constituted mainly by silica and zirconia, because it can give a cured material allowing for high contrast of X-ray photography and having high abrasion resistance.

As to the shape of the inorganic particles, there is no particular restriction. However, a spherical or nearly spherical shape is preferred in order to obtain high surface smoothness and high abrasion resistance. The inorganic particles can be used per se or in an agglomerated state.

Here, "nearly spherical" means such a shape that, when a micrograph is taken for inorganic particles using a scanning electron microscope (hereinafter abbreviated as SEM) and the inorganic particles (50 or more) in the unit visual field are observed, the average of the values obtained by dividing the particle diameter of each particle in a direction perpendicular to the maximum diameter, by the maximum diameter is 0.6 or larger, preferably 0.7 or larger.

As to the method for producing the spherical or nearly spherical inorganic particles, there is no particular restriction. Industrially, they are produced generally by the so-called sol-gel process.

In the sol-gel process, first, there is prepared a solution of a hydrolyzable organic silicon compound, or a solution obtained by adding, to the former solution, a hydrolyzable organic metal compound (e.g. alkoxide) containing at least one kind of metal selected from the group consisting of metals of groups I, II, III and IV of periodic table. Then, the solution is added to an alkaline solvent which dissolves the organic silicon compound and the organic metal compound but does not dissolve reaction products substantially. Hydrolysis and condensation reactions of the organic silicon compound and the organic metal compound are conducted in the alkaline solution, whereby reaction products separate out. Lastly, the separated-out materials are dried.

The inorganic oxide, etc. after drying, obtained by the sol-gel process may be fired at 500 to 1,000° C. in order to keep the surface stability. In the firing, part of the inorganic oxide may cause agglomeration. In this case, it is preferred that the agglomerated particles are disintegrated using a jet mill, a vibration ball mill or the like, then the grain size is adjusted, and the particles obtained are used. Even by such an operation, it is difficult to return the agglomerated particles completely to the original single-particle state before agglomeration. Therefore, when the above-mentioned heat treatment is conducted, there are ordinarily obtained inorganic particles which are a mixture of primary particles (spherical or nearly spherical inorganic particles) and an agglomerated material thereof.

As to the particle diameter of the inorganic particles compounded in the organic filler, there is no particular restriction. The average particle diameter of primary particles is preferably 0.001 to 1 μm in order to allow, for example, the cured material of the composite resin obtained to have high surface smoothness, high abrasion resistance and high mechanical strength.

Preferably, the inorganic particles are subjected to a treatment for surface hydrophobicity, in order to improve the dispersibility in organic resin. As to the method for the treatment for surface hydrophobicity, there is no particular restriction and a known method can be employed with no restriction. As the agent used for the treatment for surface hydrophobicity, there can be mentioned known silane coupling agents each composed of an organic silicon compound such as methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane, hexamethyldisilazane, or the like.

A representative method for the treatment for surface hydrophobicity is shown below. In this method, first, an appropriate solvent and a silane coupling agent are added to inorganic particles, and the mixture is ground in a ball mill or the like to disperse and mix the inorganic particles in and with the solvent. Then, the solvent is distilled off using an evaporator or a spray drier, followed by heating at 50 to 150° C.

As other method for the treatment for surface hydrophobicity, there can be mentioned, for example, a method of subjecting inorganic particles and the above-mentioned agent used for the treatment for surface hydrophobicity, to heating and refluxing in a solvent (e.g. alcohol) at 50 to 150° C. for about several hours.

As to the use amount of the agent for surface hydrophobicity, used in the above reaction, there is no particular restriction. The optimum level of the use amount of the agent for surface hydrophobicity is determined by beforehand confirming, by an experiment, the mechanical properties, etc. of the photopolymerizable composition obtained. A preferred range of the use amount of the agent for surface hydrophobicity is ordinarily 1 to 10 parts by mass relative to 100 parts by mass of the inorganic particles.

Incidentally, the inorganic particles may be used as a mixture of a plurality of kinds different in grain size distribution and material.

The use amount of the inorganic particles in the inorganic-containing organic filler is determined depending upon the mechanical strength required for the cured material of the photopolymerizable composition comprising the inorganic-containing organic filler. When the use amount of the inorganic particles is too large, it is difficult to homogeneously disperse the inorganic particles in the inorganic-containing organic filler. Therefore, the use amount of the inorganic particles generally is preferably 60 to 1,900 parts by mass, more preferably 150 to 900 parts by mass relative to 100 parts by mass of the raw material monomer of organic filler (in other words, 100 parts by mass of the organic resin obtained by polymerization of the monomer).

In the present invention, the use amount of the organic filler (C) in the photopolymerizable composition is determined depending upon the fluorescence imparted to the photopolymerizable composition, or, when the organic filler is the inorganic-containing organic filler, depending upon the mechanical strength imparted to the photopolymerizable composition.

The amount of the phthalate ester fluorescent agent contained in the organic filler (C) is preferably 0.001 to 2 parts by mass, more preferably 0.02 to 1 mass part relative to 100 parts by mass of the radical-polymerizable monomer (A), from the standpoint of imparting sufficient fluorescence to the photopolymerizable composition and, particularly obtaining a beautiful cured material when the photopolymerizable composition is used as a dental restorative material.

Particularly when the phthalate ester fluorescent agent contained in the organic filler (C) is 0.01 mass part or more relative to 100 parts by mass of the radical-polymerizable monomer (A), as compared with a conventional case of adding the phthalate ester fluorescent agent per se to the photopolymerizable composition, the reduction in polymerization activity during storage can be suppressed more strikingly. In consideration of these matters, the use amount of the organic filler (C) in the photopolymerizable composition ordinarily is preferably 50 to 700 parts by mass, more preferably 100 to 500 parts by mass relative to 100 parts by mass of the radical-polymerizable monomer (A).

The photopolymerizable composition of the present invention may comprise a known polymerization initiator other than the photopolymerization initiator (B) as long as the effect of the present invention is not impaired. As the other polymerization initiator, there can be mentioned organic peroxides such as benzoyl peroxide, cumene hydroperoxide and the like; +IV-valent or +V-valent vanadium compounds such as vanadium (IV) oxide acetylacetonate, bis(maltolate) oxovanadium (IV) and the like; arylborate compounds such as sodium tetraphenylboron, triethanolamine salt of tetraphenylboron, dimethyl-p-toluidine salt of tetraphenylboron, sodium tetrakis(p-fluorophenyl)boron, sodium butyltri(p-fluorophenyl)boron and the like; coumarin type coloring matters such as 3,3'-carbonylbis(7-diethylamino)coumarin, 7-hydroxy-4-methyl-coumarin and the like; acylphosphine oxides such as bis(2,4,6-trimethylbenzoyl)-phenylphosphine oxide, bis(2,6-dimethoxybenzoyl)-2,4,4-trimethylpentylphosphine oxide and the like; benzoin alkyl ethers such as benzoin methyl ether, benzoin ethyl ether, benzoin isopropyl ether and the like; thioxanthone derivatives such as 2,4-diethoxythioxanthone, 2-chlorothioxanthone, methylthioxanthone and the like; benzophenone derivatives such as benzophenone, p,p'-dimethylaminobenzophenone, p,p'-methoxybenzophenone and the like; and so forth.

The use amount of the arylborate compound or the organic peroxide is preferably as small as possible in order to obtain high stability to environmental light. The coloring matter such as coumarin type, when used in such an amount that acts as a polymerization initiator, affects greatly on the color of the photopolymerizable composition obtained. In this case, if such a photopolymerizable composition is used as a photocurable composite resin for which high beauty is required, the composition tends to give a color different from teeth.

In the photopolymerizable composition of the present invention, there may be compounded, depending upon its application purpose, an inorganic filler, water, an organic solvent, a thickening agent, etc. as long as the properties of the composition are not reduced. In this case, as the inorganic filler, there can be used, with no restriction, an inorganic filler composed of an inorganic compound, known as a filler for dental composite resin. As examples of representative inorganic filler, there can be mentioned inorganic oxides (e.g. inorganic particles) compounded in the above-mentioned inorganic-containing organic filler, and glasses such as lanthanum glass, barium glass, strontium glass and the like. As necessary, there may further be compounded inorganic particles of silicate glass, fluoroaluminosilicate glass and the like. These inorganic particles are known in dental treatment as cation releasing inorganic particles. These inorganic fillers may be used in one kind or in admixture of two or more kinds.

The particle diameter of the inorganic filler is not particularly restricted. A filler having an average particle diameter of 0.01 μm to 100 μm, preferably 0.01 to 5 μm (such a filler is generally used in dental materials) can be used appropriately depending upon the application purpose. There is no particular restriction, either, as to the refractive index of the inorganic filler, and an inorganic filler of 1.4 to 1.7 (such an refractive index is possessed by ordinary dental inorganic fillers) can be used with no restriction. The refractive index of the inorganic filler may be appropriately set so as to meet the application purpose of the photopolymerizable composition. A plurality of inorganic fillers different in particle diameter range and refractive index may be used in combination.

Further, the inorganic filler is preferably spherical. A dental filling and restorative material produced using a spherical inorganic filler is superior because it gives a cured material of high surface smoothness.

The inorganic filler is preferably subjected to treatment for surface hydrophobicity, as in the case of the inorganic particles compounded in the inorganic-containing organic filler. By the treatment for surface hydrophobicity, the inorganic filler can have higher affinity with the radical-polymerizable monomer and the cured material obtained can have higher mechanical strength and higher water resistance.

The use amount of the inorganic filler is determined appropriately in view of the application purpose of photopolymerizable composition, the viscosity (this relates to operability) when mixed with the polymerizable monomer, the mechanical properties of cured material, etc. The use amount of the inorganic filler is generally 50 to 1,500 parts by mass, preferably 70 to 1,000 parts by mass relative to 100 parts by mass of the polymerizable monomer.

As the organic solvent which may be compounded in the photopolymerizable composition of the present invention, there can be mentioned hexane, heptane, octane, toluene, dichloromethane, methanol, ethanol, ethyl acetate, etc.

As the thickening agent which may be compounded in the photopolymerizable composition of the present invention, there can be mentioned, for example, high molecular compounds such as polyvinylpyrrolidone, carboxymethyl cellulose, polyvinyl alcohol and the like and silica of high dispersibility.

The photopolymerizable composition of the present invention is used particularly preferably as a dental filling and restorative material represented by the above-mentioned photo-curable composite resin. However, the composition is usable not only as a dental filling and restorative material but also in other application preferably. The other application includes, for example, industrial adhesive, coating, coating material, photoresist material, process material for printing, and hologram material.

As the light source for curing the photopolymerizable composition of the present invention, there can be used a known light source ordinarily used for curing of photopolymerization initiator of α-diketone type.

Besides the above light source, there can be used, with no restriction, light sources of visible light, such as carbon arc, xenon lamp, metal halide lamp, tungsten lamp, LED, helium cadmium laser, argon laser and the like. In this case, there can be exhibited more strikingly the feature of the present photopolymerizable composition that the composition is relatively stable to a weak light but is rapidly cured when irradiated with a strong light.

The time of light irradiation differs depending upon the wavelength and intensity of light source and the shape and material of cured material. Therefore, the irradiation time is preferably determined in advance by conducting a preliminary experiment. The irradiation time is ordinarily 3 seconds to 180 minutes when the above-mentioned light source is used.

EXAMPLES

The present invention is described more specifically below by way of Examples. However, the present invention is in no way restricted by these Examples. Incidentally, the abbreviations (given in parenthesis) used in the following Examples and Comparative Examples are shown below.
(1) Abbreviations
(A) Radical-Polymerizable Monomer
    2,2-Bis[(3-methacryloyloxy-2-hydroxypropyloxy)phenyl]propane (bis-GMA)
    Triethylene glycol dimethacrylate (3G)
(B) Photopolymerization Initiator
(B1) α-Diketone
    Camphorquinone (CQ)
(B2-1) Trihalomethyl group-substituted s-triazine compound
    2,4,6-Tris(trichloromethyl)-s-triazine (TCT)
    2-Phenyl-4,6-bis((trichloromethyl)-s-triazine (PBCT)
(B2-2) Diphenyl Iodonium Salt Compound
    Diphenyl iodonium hexafluorophosphoric acid (IP)
    4-Isopropyl-4'methyldiphenyl iodonium tetrakis(pentafluorophenyl) borate (IB)
(B3) Aromatic Amine Compound
    Ethyl N,N-dimethyl p-benzoate (DMBE)
    N,N-dimethyl p-toluidine (DMPT)
(B4) Tertiary Aliphatic Amine
    Triethanolamine (TEOA)
    N-methyldiethanolamine (MDEOA)
(B5) Other
    Azobisisobutyronitrile (AIBN)
Fluorescent Agent
[Phthalate Ester Fluorescent Agent]
    Dimethyl aminoterephthalate (DATP)
    Diethyl 2,5-dihydroxyterephthalate (DHTP)
[Other Fluorescent Agent]
    2,5bis(5'-tert-butylbenzoxazolyl (2))thiophene (BOTh)
Other Component
    Hydroquinone monomethyl ether (HQME)
    2-Hydroxy-4-methoxybenzophenoe (BP)
Inorganic Particles Spherical silica zirconia filler: average particle diameter of primary particles=0.2 µm, surface-treated with γ-methacryloyloxypropyltrimethoxysilane (E-1)

The following methods were used for preparation of photo-curable composite resin, preparation of organic filler or inorganic-containing organic filler, and measurement of mechanical strength of cured material.

(1) Method for Preparation of Photo-Curable Composite Resin

To a radical-polymerizable monomer were added given amounts of a photopolymerization initiator, an organic filler and/or an inorganic-containing organic filler, and/or inorganic particles. The mixture was stirred uniformly in a red-colored light to prepare each photo-curable composite resin.

(2) Method for Preparation of Organic Filler

[Inorganic Particles-Free Filler]

In 100 parts by mass of a radical-polymerizable monomer (bis-GMA/3G=60/40) were dissolved a given amount (Table 1) of a fluorescent agent and 0.5% (mass ratio) of a polymerization initiator (AIBN). The solution was heated at 95° C. for 1 hour in a nitrogen pressure (0.5 MPa), to give rise to polymerization and curing. The cured material obtained was ground using a vibration ball mill to obtain organic fillers H-1, H-2, H-3, H-4, H-5, H-6 and H-7 each having an average particle diameter of 30 µm.

[Inorganic Particles-Containing Filler]

In 100 parts by mass of a radical-polymerizable monomer (bis-GMA/3G=60/40) were dissolved a given amount (Table 1) of a fluorescent agent and 0.5% (mass ratio) of a polymerization initiator (AIBN). Thereto was added an given amount (Table 1) of inorganic particles, followed by mixing. The mixture was made into a paste in a mortar. The paste was heated at 95° C. for 1 hour in a nitrogen pressure (0.5 MPa), to give rise to polymerization and curing. The cured material obtained was ground using a vibration ball mill. The particles obtained were subjected to a treatment for surface hydrophobicity by refluxing the particles at 90° C. for 5 hours in ethanol containing 0.02 mass % of γ-methacryloyloxypropyltrimethoxysilane, whereby inorganic-containing organic fillers I-1, I-2, I-3, I-4 and I-5 each having an average particle diameter of 30 µm were obtained.

TABLE 1

| Raw material monomer of organic filler Kind and parts by mass | Fluorescent agent Kind | Addition amount/mass part | Inorganic particles Kind and parts by mass |
|---|---|---|---|
| H-1 Bis-GMA/3G = 60/40 | DATP | 0.010 | — |
| H-2 Bis-GMA/3G = 60/40 | DATP | 0.030 | — |
| H-3 Bis-GMA/3G = 60/40 | DHTP | 0.005 | — |
| H-4 Bis-GMA/3G = 60/40 | DHTP | 0.010 | — |
| H-5 Bis-GMA/3G = 60/40 | DHTP | 0.030 | — |
| H-6 Bis-GMA/3G = 60/40 | DHTP | 0.300 | — |
| H-7 Bis-GMA/3G = 60/40 | — | — | — |
| I-1 Bis-GMA/3G = 15/10 | DATP | 0.010 | E-1 75 |
| I-2 Bis-GMA/3G = 15/10 | DATP | 0.030 | E-1 75 |
| I-3 Bis-GMA/3G = 15/10 | DHTP | 0.010 | E-1 75 |
| I-4 Bis-GMA/3G = 15/10 | DHTP | 0.030 | E-1 75 |
| I-5 Bis-GMA/3G = 15/10 | — | — | E-1 75 |

Polymerization initiator: AIBN (3) Hardness (Vickers Hardness) of Cured Material There was prepared a mold made of TEFLON (registered trademark) having a hole of 6 mm (diameter)×1.0 mm (depth). A photo-curable composite resin paste was filled in the hole of the mold, and a polypropylene film was press-contacted to the hole inlet of the mold. To the polypropylene film was tightly contacted a dental light applicator [LUX•O•MAX (hereinafter abbreviated as LM, in some cases), AKEDA DENTAL, light output density: 137 mW/cm$^2$], and light irradiation was conducted for 10 seconds to prepare a cured material. The cured material was measured for hardness using a micro hardness tester (MHT-1 Model, a product of MATSUSAWA SEIKI). The measurement was conducted under the conditions of load=100 gf and load application time=30 seconds, using a Vickers indenter. The length of the diagonal of the dent formed in the test piece used was measured and the hardness of the cured material was determined.

(4) Evaluation for Storage Stability

A photo-curable composite resin prepared was stored in an incubator set at 50° C. The photo-curable composite resin after storage of 0 day, 14 days or 28 days was measured for Vickers hardness according to the method described in (3). The storage stability was evaluated from the change of Vickers hardness with time.

(5) Evaluation for Fluorescence

There was prepared a mold made of TEFLON (registered trademark) having a hole of 7 mm (diameter)×3.0 mm (depth). A photo-curable composite resin paste was filled in the hole of the mold, and a polypropylene film was press-contacted. To the polypropylene film was tightly contacted a dental light applicator (TOKUSO POWER LIGHT, TOKUYAMA DENTAL, light output density: 600 mW/cm$^2$), and light irradiation was conducted for 30 seconds to prepare a cured material.

The cured material was irradiated with an ultraviolet light using an ultraviolet applicator (MINERALIGHT LAMP, FUNAKOSI YAKUHIN, maximum absorption wavelength: 366 nm), to observe the fluorescence emitted. A case when excellent fluorescence was confirmed, was rated as "E"; a case when good fluorescence was confirmed, was rated as "G"; and a case when no fluorescence was confirmed, was rated as "X".

Examples 1 to 18, Comparative Examples 1 to 5, Reference Examples 1 to 4

100 parts by mass of a radical-polymerizable monomer (consisting of 60 parts by mass of bis-GMA and 40 parts by mass of 3G), 0.15 mass part of HQME (as a polymerization inhibitor), a photopolymerization initiator (shown in Table 2), an organic filler (shown in Table 2) and a fluorescent agent (shown in Table 2) were mixed, with stirring, in a dark place, using an agate mortar, to prepare each photo-curable composite resin of paste state. Using each paste, a cured material was prepared according to the same method as described in (3) and measured for Vickers hardness. Each paste was also evaluated for storage stability. The results are shown in Table 2.

TABLE 2

| | Photopolymerization initiator/mass part | | | Organic filler | | Fluorescent agent | | Use amount of fluorescent agent, Mass part | | Storage stability (Vickers hardness/LM) Period (days) | | |
| --- | --- | --- | --- | --- | --- | --- | --- | --- | --- | --- | --- | --- |
| | α-Diketone | Aromatic amine | Photoacid generating agent | Kind | Parts by mass | Kind | Mass part | | Fluorescence | 0 day | 14 days | 28 days |
| Ex. 1 | CQ 0.2 | DMPT 0.35 | TCT 0.20 | H-1 | 300 (0.01)* | — | — | 0.030 | E | 15 | 13 | 13 |
| Ex. 2 | CQ 0.2 | DMBE 0.35 | TCT 0.20 | H-1 | 300 (0.01) | — | — | 0.030 | E | 13 | 12 | 12 |
| Ex. 3 | CQ 0.2 | DMBE 0.35 | TCT 0.20 | H-2 | 300 (0.03) | — | — | 0.090 | E | 13 | 12 | 12 |
| Ex. 4 | CQ 0.2 | DMBE 0.35 | TCT 0.20 | H-3 | 300 (0.005) | — | — | 0.015 | G | 13 | 13 | 12 |
| Ex. 5 | CQ 0.2 | DMBE 0.35 | TCT 0.20 | H-4 | 200 (0.01) | — | — | 0.020 | E | 14 | 13 | 13 |
| Ex. 6 | CQ 0.2 | DMBE 0.35 | TCT 0.20 | H-4 | 300 (0.01) | — | — | 0.030 | E | 13 | 12 | 12 |
| Ex. 7 | CQ 0.2 | DMBE 0.35 | TCT 0.20 | H-4 | 400 (0.01) | — | — | 0.040 | E | 13 | 13 | 12 |
| Ex. 8 | CQ 0.2 | DMPT 0.35 | TCT 0.20 | H-4 | 300 (0.01) | — | — | 0.030 | E | 14 | 13 | 12 |
| Ex. 9 | CQ 0.2 | DMBE 0.35 | TCT 0.20 | H-5 | 300 (0.03) | — | — | 0.090 | E | 13 | 12 | 12 |
| Ex. 10 | CQ 0.2 | DMBE 0.35 | TCT 0.20 | H-6 | 300 (0.30) | — | — | 0.900 | E | 13 | 10 | 9 |
| Ex. 11 | CQ 0.2 | DMBE 0.35 | TCT 0.30 | H-4 | 300 (0.01) | — | — | 0.030 | E | 13 | 12 | 11 |
| Ex. 12 | CQ 0.2 | DMBE 0.35 | TCT 0.40 | H-4 | 300 (0.01) | — | — | 0.030 | E | 14 | 13 | 13 |
| Ex. 13 | CQ 0.2 | DMBE 0.35 | PBCT 0.40 | H-4 | 300 (0.01) | — | — | 0.030 | E | 14 | 13 | 12 |
| Ex. 14 | CQ 0.2 | DMBE 0.35 | IP 0.40 | H-4 | 300 (0.01) | — | — | 0.030 | E | 13 | 12 | 12 |
| Ex. 15 | CQ 0.2 | DMBE 0.35 | IB 0.40 | H-4 | 300 (0.01) | — | — | 0.030 | E | 15 | 13 | 13 |
| Ex. 16 | CQ 0.2 | DMBE 0.35 | IB 0.50 | H-4 | 300 (0.01) | — | — | 0.030 | E | 13 | 12 | 12 |
| Ex. 17 | CQ 0.2 | DMPT 0.35 | IB 0.50 | H-4 | 300 (0.01) | — | — | 0.030 | E | 14 | 13 | 13 |
| Ex. 18 | CQ 0.2 | DMBE 0.35 | IB 0.75 | H-4 | 300 (0.01) | — | — | 0.030 | E | 14 | 13 | 12 |
| Comp. Ex. 1 | CQ 0.2 | DMPT 0.35 | TCT 0.20 | H-7 | 300 (0) | DATP | 0.030 | 0.030 | E | 11 | 7 | 6 |
| Comp. Ex. 2 | CQ 0.2 | DMBE 0.35 | TCT 0.20 | H-7 | 300 (0) | DHTP | 0.030 | 0.030 | E | 12 | 9 | 7 |
| Comp. Ex. 3 | CQ 0.2 | DMBE 0.35 | TCT 0.20 | H-7 | 300 (0) | DATP | 0.030 | 0.030 | E | 11 | 9 | 7 |
| Comp. Ex. 4 | CQ 0.2 | DMBE 0.35 | TCT 0.20 | H-7 | 300 (0) | DHTP | 0.070 | 0.070 | E | 12 | 7 | 6 |
| Comp Ex. 5 | CQ 0.2 | DMBE 0.35 | IB 0.50 | H-7 | 300 (0) | DHTP | 0.030 | 0.030 | E | 11 | 9 | 6 |
| Ref. Ex. 1 | CQ 0.2 | DMBE 0.35 | TCT 0.20 | H-7 | 300 (0) | BOTh | 0.030 | 0.030 | E | 13 | 12 | 12 |
| Ref. Ex. 2 | CQ 0.2 | DMBE 0.35 | | H-7 | 300 (0) | DATP | 0.030 | 0.030 | E | 12 | 11 | 11 |
| Ref. Ex. 3 | CQ 0.2 | DMBE 0.35 | | H-7 | 300 (0) | DHTP | 0.030 | 0.030 | E | 12 | 12 | 11 |
| Ref. Ex. 4 | CQ 0.2 | DMBE 0.35 | TCT 0.20 | H-7 | 300 (0) | — | — | — | X | 13 | 12 | 12 |

Composition of radical-polymerizable monomer: bis-GMA/3G = 60/40 (parts by mass)
Polymerization inhibitor: HQME = 0.15 (mass part)
Ultraviolet absorber: BP = 2.0 (parts by mass)
*Use amount (mass part) of fluorescent agent per 100 parts by mass of an organic resin constituting an organic filler As is understood from the results shown in Examples 1 to 18 and Comparative Examples 1 to 5, the hardness after 28 days of storage was maintained 80% or more of the initial value in Examples 1 to 9 and 11 to 18 where a fluorescent agent was compounded in an organic filler in an amount of 0.005 to 0.05 mass part relative to 100 parts by mass of an organic resin. Also, even when the use amount of a fluorescent agent was a little large at 0.3 mass part relative to 100 parts by mass of an organic resin, the hardness after 28 days of storage was as high as 69% of the initial value.

Meanwhile, in Comparative Examples where a fluorescent agent was not compounded in an organic filler and was compounded per se in a photopolymerizable composition, the hardness after storage was reduced to about 65% of the initial value.

Incidentally, as shown in Reference Example 1 using a fluorescent agent other than phthalate ester type and in Reference Examples 2 and 3 using a photopolymerization initiator containing no photoacid generating agent, the hardness after storage could be kept at 80% or more of the initial value. Incidentally, the fluorescence confirmed in Reference Example 1 had a color different from the color of teeth. Accordingly, by using this photo-curable composite resin photopolymerizable composition as a dental filling and restorative material, the tooth aesthetic color was inferior.

Examples 19 to 24, Comparative Examples 6 to 10

An inorganic-containing organic filler containing inorganic particles was used an organic filler, as shown in Table 3. Each photo-curable composite resin paste was prepared in the same manner as in Example 1, and measured for properties. The results are shown in Table 3. State of fluorescence emission and storage stability were good.

TABLE 3

| | Photopolymerization initiator/mass part | | | Organic filler | | Fluorescent agent | | Use amount of fluorescent agent Mass part | | Storage stability (Vickers hardness/LM) Period (days) | | |
| --- | --- | --- | --- | --- | --- | --- | --- | --- | --- | --- | --- | --- |
| | α-Diketone | Aromatic amine | Photoacid generating agent | Kind | Parts by mass | Kind | Mass part | | Fluorescence | 0 day | 14 days | 28 days |
| Ex. 19 | CQ 0.2 | DMPT 0.35 | TCT 0.20 | I-1 | 300 (0.01) | — | — | 0.030 | E | 16 | 14 | 13 |
| Ex. 20 | CQ 0.2 | DMPT 0.35 | TCT 0.20 | I-2 | 300 (0.01) | — | — | 0.030 | E | 16 | 15 | 14 |
| Ex. 21 | CQ 0.2 | DMBE 0.35 | TCT 0.20 | I-1 | 300 (0.01) | — | — | 0.030 | E | 15 | 13 | 13 |
| Ex. 22 | CQ 0.2 | DMBE 0.35 | TCT 0.20 | I-2 | 300 (0.01) | — | — | 0.030 | E | 15 | 15 | 13 |
| Ex. 23 | CQ 0.2 | DMBE 0.35 | IB 0.50 | I-1 | 300 (0.01) | — | — | 0.030 | E | 16 | 15 | 14 |

TABLE 3-continued

| | Photopolymerization initiator/mass part | | | Organic filler | | | Fluorescent agent | | Use amount of fluorescent agent Mass part | Fluorescence | Storage stability (Vickers hardness/LM) Period (days) | | |
|---|---|---|---|---|---|---|---|---|---|---|---|---|---|
| | α-Diketone | Aromatic amine | Photoacid generating agent | Kind | Parts by mass | | Kind | Mass part | | | 0 day | 14 days | 28 days |
| Ex. 24 | CQ 0.2 | DMBE 0.35 | IB 0.50 | I-2 | 300 | (0.01) | — | — | 0.030 | E | 16 | 16 | 15 |
| Comp. Ex. 6 | CQ 0.2 | DMPT 0.35 | TCT 0.20 | I-3 | 300 | (0) | DATP | 0.030 | 0.030 | E | 14 | 11 | 9 |
| Comp. Ex. 7 | CQ 0.2 | DMBE 0.35 | TCT 0.20 | I-3 | 300 | (0) | DATP | 0.030 | 0.030 | E | 13 | 11 | 9 |
| Comp. Ex. 8 | CQ 0.2 | DMBE 0.35 | TCT 0.20 | I-3 | 300 | (0) | DHTP | 0.030 | 0.030 | E | 13 | 10 | 8 |
| Comp. Ex. 9 | CQ 0.2 | DMBE 0.35 | IB 0.50 | I-3 | 300 | (0) | DATP | 0.030 | 0.030 | E | 14 | 11 | 8 |
| Comp. Ex. 10 | CQ 0.2 | DMBE 0.35 | IB 0.50 | I-3 | 300 | (0) | DHTP | 0.030 | 0.030 | E | 14 | 11 | 7 |

Composition of radical-polymerizable monomer: bis-GMA/3G = 60/40 (parts by mass)
Polymerization inhibitor: HQME = 0.15 (mass part)
Ultraviolet absorber: BP = 2.0 (parts by mass)

Examples 25 to 32, Comparative Examples 11 to 16

As shown in Table 4, the kind of each component of photopolymerization initiator was varied. Each photo-curable composite resin paste was prepared in the same manner as in Example 1, and measured for properties. The results are shown in Table 4.

TABLE 4

| | Photopolymerization initiator/mass part | | | | Organic filler | | Inorganic particles | | Fluorescent agent | | Use amount of fluorescent agent Mass part |
|---|---|---|---|---|---|---|---|---|---|---|---|
| | α-Diketone | Aromatic amine | Aliphatic amine | Photoacid generating agent | Kind | Parts by mass | Kind | Parts by mass | Kind | Mass part | |
| Ex. 25 | CQ 0.2 | DMPT 0.35 | TEOA 0.20 | TCT 0.30 | H-2 | 180 (0.03) | E-1 | 120 | — | — | 0.054 |
| Ex. 26 | CQ 0.2 | DMBE 0.35 | TEOA 0.20 | TCT 0.30 | H-2 | 180 (0.03) | E-1 | 120 | — | — | 0.054 |
| Ex. 27 | CQ 0.2 | DMBE 0.35 | MDEOA 0.20 | TCT 0.30 | I-2 | 180 (0.03) | E-1 | 120 | — | — | 0.054 |
| Ex. 28 | CQ 0.2 | DMBE 0.35 | MDEOA 0.20 | TCT 0.30 | H-5 | 180 (0.03) | E-1 | 120 | — | — | 0.054 |
| Ex. 29 | CQ 0.2 | DMBE 0.35 | MDEOA 0.20 | IP 0.50 | I-2 | 180 (0.03) | E-1 | 120 | — | — | 0.054 |
| Ex. 30 | CQ 0.2 | DMBE 0.35 | TEOA 0.20 | IP 0.50 | I-2 | 180 (0.03) | E-1 | 120 | — | — | 0.054 |
| Ex. 31 | CQ 0.2 | DMBE 0.35 | MDEOA 0.20 | IB 0.50 | I-4 | 180 (0.03) | E-1 | 120 | — | — | 0.054 |
| Ex. 32 | CQ 0.2 | DMBE 0.35 | MDEOA 0.20 | IP 0.50 | H-5 | 180 (0.03) | E-1 | 120 | — | — | 0.054 |
| Comp. Ex. 11 | CQ 0.2 | DMBE 0.35 | TEOA 0.20 | TCT 0.30 | I-5 | 180 | E-1 | 120 | DATP | 0.054 | 0.054 |
| Comp. Ex. 12 | CQ 0.2 | DMBE 0.35 | MDEOA 0.20 | TCT 0.30 | I-5 | 180 | E-1 | 120 | DHTP | 0.054 | 0.054 |
| Comp. Ex. 13 | CQ 0.2 | DMBE 0.35 | MDEOA 0.20 | IP 0.50 | I-5 | 180 | E-1 | 120 | DATP | 0.054 | 0.054 |
| Comp. Ex. 14 | CQ 0.2 | DMBE 0.35 | TEOA 0.20 | IP 0.50 | I-5 | 180 | E-1 | 120 | DATP | 0.054 | 0.054 |
| Comp. Ex. 15 | CQ 0.2 | DMBE 0.35 | MDEOA 0.20 | IB 0.50 | I-5 | 180 | E-1 | 120 | DHTP | 0.054 | 0.054 |
| Comp. Ex. 16 | CQ 0.2 | DMBE 0.35 | MDEOA 0.20 | IB 0.50 | H-7 | 180 | E-1 | 120 | DHTP | 0.054 | 0.054 |

| | Fluorescence | Storage stability (Vickers hardness/LM) Period (days) | | |
|---|---|---|---|---|
| | | 0 day | 14 days | 28 days |
| Ex. 25 | E | 30 | 27 | 26 |
| Ex. 26 | E | 30 | 27 | 26 |
| Ex. 27 | E | 31 | 28 | 26 |
| Ex. 28 | E | 27 | 25 | 24 |
| Ex. 29 | E | 29 | 25 | 24 |
| Ex. 30 | E | 29 | 26 | 25 |
| Ex. 31 | E | 29 | 25 | 24 |
| Ex. 32 | E | 29 | 25 | 24 |
| Comp. Ex. 11 | E | 29 | 21 | 20 |
| Comp. Ex. 12 | E | 31 | 23 | 21 |
| Comp. Ex. 13 | E | 27 | 20 | 17 |
| Comp. Ex. 14 | E | 27 | 21 | 16 |
| Comp. Ex. 15 | E | 28 | 21 | 18 |
| Comp. Ex. 16 | E | 25 | 20 | 17 |

Composition of radical-polymerizable monomer: bis-GMA/3G = 60/40 (parts by mass)
Polymerization inhibitor: HQME = 0.15 (mass part)
Ultraviolet absorber: BP = 2.0 (parts by mass)

The invention claimed is:

1. A photopolymerizable composition comprising
   (A) a radical-polymerizable monomer,
   (B) a photopolymerization initiator comprising
      (B1) an α-diketone compound,
      (B2) a photoacid generating agent, and
      (B3) an aromatic amine compound, and
   (C) an organic filler comprising a cured organic resin material obtained by polymerizing a polymerizable monomer and a phthalate ester fluorescent agent contained in the matrix.

2. The photopolymerizable composition according to claim 1, wherein the α-diketone compound (B1) is a camphorquinone.

3. The photopolymerizable composition according to claim 1, wherein the photoacid generating agent (B2) is selected from the group consisting of a s-triazine compound substituted with trihalomethyl group and a diaryl iodonium salt compound.

4. The photopolymerizable composition according to claim 1, wherein the photopolymerization initiator (B) further comprises (B4) a tertiary aliphatic amine compound having a tertiary amino group in which three saturated aliphatic groups are bonded to the nitrogen atom and at least two of the saturated aliphatic groups bonding to the nitrogen atom have each an electron attractive group.

5. The photopolymerizable composition according to claim 1, wherein the phthalate ester fluorescent agent is represented by

[formula 1]

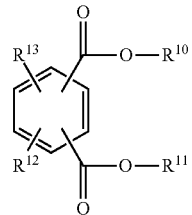

wherein, in the formula, $R^{10}$ and $R^{11}$ are each independently an alkyl group; $R^{12}$ is a hydrogen atom, an amino group, or a hydroxyl group; and $R^{13}$ is an amino group, or a hydroxyl group.

6. The photopolymerizable composition according to claim 1, wherein the organic filler (C) containing a phthalate ester fluorescent agent is an inorganic-containing organic filler in which inorganic particles are compounded in an amount of 150 to 600 parts by mass relative to 100 parts by mass of an organic resin.

7. A dental restorative material containing a photopolymerizable composition according to claim 1.

* * * * *